United States Patent [19]

Chao

[11] Patent Number: 4,783,554

[45] Date of Patent: Nov. 8, 1988

[54] ALKYLATION OF AMINE COMPOUNDS

[75] Inventor: Kuo-Hua Chao, Houston, Tex.

[73] Assignee: Shell Oil Company, Houston, Tex.

[21] Appl. No.: 940,385

[22] Filed: Dec. 10, 1986

[51] Int. Cl.$^4$ .............................................. C07C 85/00
[52] U.S. Cl. .................................... 564/463; 564/467; 564/469; 564/470; 585/708
[58] Field of Search ............... 564/463, 467, 469, 470; 585/708

[56] References Cited

U.S. PATENT DOCUMENTS

| | | | |
|---|---|---|---|
| 2,751,423 | 6/1956 | Conn | 585/708 |
| 4,430,513 | 2/1984 | Homeier | 564/469 |
| 4,562,291 | 12/1985 | Wilson, Jr. et al. | 564/463 |
| 4,645,837 | 2/1987 | Laine et al. | 564/470 |

OTHER PUBLICATIONS

Kirk-Othmer, *Encyclopedia of Chemical Technology* 3d ed., vol. 2, pp. 204–214, vol 11, pp. 269–280 (1978).

*Primary Examiner*—Richard L. Raymond
*Assistant Examiner*—John A. Sopp

[57] ABSTRACT

Alkylamines are self-alkylated to longer carbon chain alkylamines using a catalyst mixture comprising of aluminum chloride in combination with cobalt and/or ruthenium carbonyl.

9 Claims, No Drawings

ALKYLATION OF AMINE COMPOUNDS

FIELD OF THE INVENTION

The present invention relates to the catalytic synthesis of longer chain alkylamines by the oligomerization or self-alkylation of mono-, di- and trialkylamines.

BACKGROUND OF THE INVENTION

The common method of alkylating organic compounds is by using alkylating agents such as olefins or alkylhalides in the presence of a Friedel Crafts catalyst. When amines are used as alkylating agents with Friedel Crafts catalysts, the alkylation reaction is severely inhibited by the fact that the amine poisons the catalyst by the formation of an acid-base compound.

U.S. Pat. No. 4,430,513, issued Feb. 7, 1984, discloses one method in which alkylamines can satisfactorily be used as alkylating agents. Specifically, this patent teaches the self-alkylation of alkylamine compounds which contain at least two alkyl substituents containing from about 2 to 6 carbon atoms. The alkylamine compounds are alkylated in the presence of a rhodium or cobalt carbonyl or a rhodium or cobalt compound which is capable of forming a carbonyl under alkylation conditions.

U.S. Pat. No. 4,562,291, issued Dec. 31, 1985, discloses the self-alkylation of mono-, di- and trialkylamines using a catalyst mixture comprising a tetrafluoroborate salt and a ruthenium, an osmium or an iridium-containing compound.

The oligomerized alkylamines prepared by the process of the instant invention are useful for preparing detergent products and disinfectant products.

SUMMARY OF THE INVENTION

The present invention involves a process for the catalytic synthesis of long chain alkylamines. Specifically, mono-, di- or trialkylamines are oligomerized or self-alkylated to form longer chain alkylamines by contacting the mono-, di- and/or trialkylamines with a catalyst mixture comprising aluminum chloride and a cobalt and/or ruthenium carbonyl or cobalt and/or ruthenium-containing salt(s) capable of forming a carbonyl under alkylation conditions. The mole ratio of cobalt and/or ruthenium carbonyl to aluminum chloride typically ranges from about 1:1 to about 1:100. A particular advantage of the instant invention is that it can be used to convert alkylamines to their mono-alkylated amine products in high yield. Selectivities of the instant catalyst combinations result in the product amines being predominately (i.e., greater than about 50%) the mono-alkylates. This can result in simpler product mixes with concomitant lower separation costs.

DETAILED DESCRIPTION OF THE INVENTION

The present invention provides a process for synthesizing long chain alkylamines by self-alkylation or oligomerization of shorter chain alkylamines. Any typical alkylamine can be oligomerized in accordance with the present invention. The invention is particularly suitable for alkylating trialkylamines. Oligomerization produces a mixture of various longer chain alkylamines. In a preferred embodiment, the instant process converts an amine predominately to its next higher homologue i.e., a mono-alkylated amine. For example, triethylamine is converted predominately to butyldiethylamine.

The reaction is run in the presence of a catalyst mixture comprising aluminum chloride and a cobalt carbonyl, a ruthenium carbonyl or mixtures thereof or a cobalt-containing compound, a ruthenium-containing compound or a mixture thereof which is capable of being converted to carbonyls under alkylation conditions. The mole ratio of cobalt and/or ruthenium carbonyl to aluminum chloride in the catalyst mixture will range from about 1:1 to about 1:100, more preferably from about 1:1 to about 1:20.

Generally, carbon monoxide is added to the reaction mixture. While carbon monoxide is not absolutely needed when the carbonyls are used in the reaction mixture, its presence adds to the stability of the catalyst mixture. When cobalt and ruthenium compounds are used, carbon monoxide is added to the reaction mixture to convert the compounds to the carbonyls. The presence of hydrogen is not required in the reaction mixture. Its presence has no adverse effects and the use of syngas to provide the reaction mixture with carbon monoxide will also provide hydrogen.

The oligomerization is a liquid phase reaction. It is preferably carried out in the presence of a solvent, preferably an amine solvent. Most preferably the solvent is an aliphatic amine. Preferably the reactant amines are used as the reaction solvents. Other solvents such as alcohols, ethers, aromatics or paraffins can be used, but are less desirable.

The oligomerization reaction is typically carried out at a temperature range of from about 50° C. to about 300° C., more preferably from about 150° C. to about 250° C. Procedures will typically run from about 1 atmosphere to about 500 atmospheres, more preferably from about 1 to about 300 atmospheres and more preferably from about 20 to about 100 atmospheres.

The process of the instant invention may be accomplished in either a batch or continuous type operation. For example, when a batch type operation is to be employed, a quantity of the catalyst and amine compound along with an organic solvent, if one is to be used, will be placed in a pressure-resistant apparatus such as an autoclave of the stirring, mixing or rotating type. Following the addition of the catalyst and starting material, the apparatus is sealed, flushed with an inert gas such as nitrogen, and pressurized to the desired operating pressure with carbon monoxide and optionally hydrogen. Upon reaching the desired operating pressure, the apparatus is then heated to a predetermined operating temperature and maintained thereat for the desired residence time which may range from about 0.5 up to about 20 hours or more in duration. Upon completion of the desired residence time, heating is discontinued and after the apparatus and contents thereof have returned to room temperature, the excess pressure is discharged, the apparatus is opened, and the reaction mixture is recovered therefrom. After separation of the product mix from the catalyst, the former may then be subjected to conventional means of separating the components of said mix, said means including fractional distillation, fractional crystallization, etc.

It is also contemplated within the scope of this invention that the alkylation of the alkylamine compound may be accomplished in a continuous manner of operation. When such a type of operation is employed, the starting material comprising the alkylamine is continuously charged to an apparatus which is maintained at the proper operating conditions of temperature and pressure. In addition, the catalyst which is to be employed as well as any solvent is also continuously charged to the reaction apparatus either through separate lines or, if so desired, the components of the reaction mixture may be admixed prior to entry into the reaction apparatus and the resulting mixture charged thereto in a single stream. After passage through the apparatus for a predetermined period of time, the reactor effluent is continuously withdrawn and subjected to conventional means of separation whereby the product mix is separated from the catalyst and any unreacted starting material that is to be recycled to the reaction apparatus to form a portion of the feedstock, while the product mix is subjected to further distillation to recover the various components of said mix.

The process of this invention is further described by the following illustrative embodiments which are provided for illustration and are not to be construed as limiting the invention.

EXAMPLE 1

To a 100 cc stainless steel screw top autoclave was added 29.0 grams of triethylamine, 0.243 grams of aluminum chloride and 0.117 grams of triruthenium dodecacarbonyl, the molar ratio of triethylamine to ruthenium carbonyl to aluminum chloride being 1570:1:10. The autoclave was sealed under inert atmosphere and flushed with carbon monoxide, following which the autoclave was pressurized to 50 atmospheres with carbon monoxide. Thereafter, the autoclave was heated to a temperature of 220° C. and maintained there for a period of 18 hours. At the end of this period, heating was discontinued and the autoclave was allowed to return to room temperature. The excess pressure was discharged, the autoclave was opened, and the reaction product comprising an orange liquid was recovered. The product was analyzed by means of gas liquid chromatography and mass spectroscopy. This analysis determined that there had been a 67.0%w conversion of the triethylamine and that the triethylamine which had been converted to higher alkylamines (50%) was converted with the selectivity shown in Table I below.

TABLE I

| Alkylated Product | Weight Percent |
|---|---|
| butyldiethylamine | 73.1 |
| hexyldiethylamine | 5.3 |
| ethyldibutylamine | 15.8 |

EXAMPLE 2

The above experiment was repeated using 0.062 grams of dicobalt octacarbonyl instead of Ru$_3$(CO)$_{12}$, providing a triethylamine:Co$_2$(CO)$_8$:AlCl$_3$ ratio of 1570:1:10. Analysis determined that there had been a 5%w conversion of the triethylamine and that the triethylamine which had been converted to higher alkylamines (50%) was converted with the selectivity shown in Table II below.

TABLE II

| Alkylated Product | Weight Percent |
|---|---|
| butyldiethylamine | 91 |
| hexyldiethylamine | 8 |
| ethyldibutylamine | 1 |

COMPARATIVE EXAMPLE A

Example 1 above was repeated except that as catalyst only aluminum chloride was used. The mole ratio of (CH$_3$CH$_2$)$_3$N:AlCl$_3$ was 1570:10. Analysis determined that there had only been a 2%w conversion of the triethylamine and that the triethylamine which had been converted to higher alkylamines (50%) was converted with a selectivity to butyldiethylamine of greater than 95%w.

COMPARATIVE EXAMPLE B

Example 1 above was repeated except that as catalyst only triruthenium dodecacarbonyl was used. The mole ratio of (CH$_3$CH$_2$)$_3$N:Ru$_3$(CO)$_{12}$ was 1570:1. Analysis determined that there had only been a 2%w conversion of the triethylamine and that the triethylamine which had been converted to higher alkylamines (50%) was converted with the following selectivities: butyldiethylamine-92%w and hexyldiethylamine-7%w.

COMPARATIVE EXAMPLE C

Example 2 above was repeated except that as catalyst only, dicobalt octacarbony was used. The mole ratio of (CH$_3$CH$_2$)$_3$N:Co$_2$(CO)$_8$ was 1570:1. Analysis determined that there had been a 19%w conversion of the triethylamine but that the triethylamine which had been converted to higher alkylamines (50%) was converted with the following selectivities: butyldiethylamine-41%w; hexyldiethylamine-22%w; ethyldibutylamine-2%w; diisooctylamine-12%w and diisodecylamine-6%w.

I claim:

1. A process for the oligomerization of alkylamines to produce longer carbon chain alkylamines which process comprises contacting said alkylamines at a temperature of from about 50° C. to about 300° C. with a catalyst mixture comprising aluminum chloride and a component selected from a ruthenium carbonyl, a ruthenium-containing compound capable of being converted to a carbonyl under oligomerization conditions and mixtures thereof.

2. The process of claim 1 wherein the ruthenium carbonyl is triruthenium dodecacarbonyl.

3. The process of claims 1, or 2 wherein the mole ratio of ruthenium carbonyl to aluminum chloride ranges from about 1:1 to about 1:100.

4. The process of claims 1, or 2 wherein carbon monoxide is added to the oligomerization mixture.

5. The process of claims 1, or 2 wherein the temperature ranges from about 175° C. to about 250° C.

6. The process of claims 1, or 2 wherein the alkylamine is triethylamine and the longer carbon chain product amine consists predominately of butyldiethylamine.

7. The process of claims 1, or 2 wherein the longer carbon chain amine consists predominately of monoalkylated amine.

8. The process of claims 1, or 2 wherein the pressure is maintained between about 1 and about 500 atmospheres.

9. A process for preparing butyldiethylamine which process comprises oligomerizing triethylamine by contacting said triethylamine at a temperature of from about 175° C. to about 250° C. with a catalyst mixture comprising aluminum chloride and a component selected from a ruthenium carbonyl, a ruthenium-containing compound capable of being converted to a carbonyl under oligomerization conditions and mixtures thereof wherein the ratio of ruthenium carbonyl to aluminum chloride ranges from about 1:1 to about 1:100.

* * * * *